United States Patent
Akira et al.

(10) Patent No.: US 7,557,258 B2
(45) Date of Patent: Jul. 7, 2009

(54) ENDOTOXIN-NONRESPONSIVE MODEL ANIMAL

(75) Inventors: Shizuo Akira, Osaka (JP); Masahiro Yamamoto, Osaka (JP)

(73) Assignee: Japan Science and Technology Agency, Kawaguchi-Shi, Saitama (JP)

(*) Notice: Subject to any disclaimer, the term of this patent is extended or adjusted under 35 U.S.C. 154(b) by 0 days.

(21) Appl. No.: 10/573,212

(22) PCT Filed: Sep. 29, 2004

(86) PCT No.: PCT/JP2004/014220

§ 371 (c)(1),
(2), (4) Date: Sep. 21, 2006

(87) PCT Pub. No.: WO2005/030269

PCT Pub. Date: Apr. 7, 2005

(65) Prior Publication Data

US 2007/0143869 A1    Jun. 21, 2007

(30) Foreign Application Priority Data

Sep. 29, 2003    (JP) ............................. 2003-338013

(51) Int. Cl.
*A01K 67/027*    (2006.01)
*G01N 33/00*    (2006.01)
*C12N 5/06*    (2006.01)
*C12N 5/10*    (2006.01)

(52) U.S. Cl. .............................. 800/18; 800/3; 435/354

(58) Field of Classification Search ....................... None
See application file for complete search history.

(56) References Cited

U.S. PATENT DOCUMENTS 6,660,906 B1    12/2003    Tsichlis

FOREIGN PATENT DOCUMENTS

WO    WO 02/053737 A1    7/2002

OTHER PUBLICATIONS

Wanecek et al., 2000, European Journal of Pharmacology, 407: 1-15.*
Doetschmann, 1999, Lab. Animal Sci., 49: 137-143.*
Moens et al., 1993, Development, 119: 485-499.*
Jacks et al., 1992, Nature, 359: 295-300.*
Kuehn et al., 1987, Nature, 326: 295-298.*
Jaenisch, 1988, Science, 240: 1468-1474.*
Racay, 2002, Bratisl Lek Listy, 103: 121-126.*
Jakel et al., 2004, Nature Reviews: Genetics, 5: 136-144.*
Gerlai, 1996, Trends Neurosci, 19: 177-181.*
Pearson, 2002, Nature, 415: 8-9.*
Murray, et al., 1999, Transgenic Animals in Agriculture, CAB International: Oxon, pp. 58-61.*
Denning and Priddle, 2003, Reproduction, 126: 1-11.*
Bin, L.H., et al., "TIRP, a Novel Toll/Interleukin-1 Receptor (TIR) Domain-Containing Adapter Protein Involved in TIR Signaling," *The Journal of Biological Chemistry*, 2000, pp. 24526-24532, vol. 278(27).
International Search Report for PCT/JP2004/014220 completed Oct. 26, 2004.
Hoebe, et al., "Identification of Lps2 as a key transducer of MyD88-independent TIR signaling," *Nature*, Aug. 2003, pp. 743-748, vol. 424.
Yamamoto, et al., "TRAM is specifically involved in the Toll-like receptor 4-mediated MyD88-independent signaling pathway," *Nature Immunology*, Nov. 2003, pp. 1144-1150, vol. 4 No. 11.
International Search report dated Mar. 12, 2007.

* cited by examiner

*Primary Examiner*—Joanne Hama
(74) *Attorney, Agent, or Firm*—Alston & Bird LLP (57) ABSTRACT

The present invention is to provide a non-human animal model non-responsive especially to endotoxin being a Gram-negative bacteria cell wall fraction, which is useful to elucidate the function of TIR domain-containing TRIF-related adaptor molecule (TRAM); and a method for screening substances promoting or suppressing responses to ligands recognized by TLR4 with the use of the non-human animal model non-responsive to endotoxin; and the like. Mice non-responsive to the endotoxin wherein a part or a whole of Tram genes on their chromosome are deleted, the function to express TRAM which is expressed in wild-types is lacked, and the responsiveness to ligands recognized by TLR4 is specifically impaired; is used for screening substances promoting or suppressing responses to ligands recognized by TLR4.

5 Claims, 5 Drawing Sheets

ENDOTOXIN-NONRESPONSIVE MODEL ANIMAL

TECHNICAL FIELD

The present invention relates to a non-human animal wherein the function of TRIF-related adaptor molecule (TRAM) genes mediating signaling of Toll-like receptors (TLR) is lacked, especially to a TRAM-knockout mouse nonresponsive to ligands recognized by TLR4 such as endotoxin; and to a method for screening substances promoting or suppressing response to ligands recognized by TLR4 by using these.

BACKGROUND ART

Toll genes are associated with determination of dorsoventral axis in the embryogenesis of Drosophilia (e.g., see Cell 52, 269-279, 1988; Annu. Rev. Cell Dev. Biol. 12, 393-416, 1996), and with innate immunity detecting invading pathogens in adult body (e.g., see Nature 406, 782, 2000; Nat. Immunol. 2, 675, 2001; Annu. Rev. Immunol. 20, 197, 2002), and the Toll is a type I transmembrane receptor having Leucine-rich repeat (LRR) in extracellular domains. Among cytokines being signaling substances between cells that play an important role in immunoreaction and response during infection, hematogenesis, viral infection, and impairment of tumor cell, cytokine transmitting signals between lymphocytes is called Interleukin (hereinafter referred to as "IL"). It has been clarified that the intracytoplasmic domain of the type I transmembrane receptor is highly homologous with the intracytoplasmic domain of mammalian IL-1 receptor (IL-1R) (e.g., see Nature 351, 355-356, 1991; Annu. Rev. Cell Dev. Biol. 12, 393-416, 1996; J. Leukoc. Biol. 63, 650-657, 1998).

Recently, mammal homologue of Toll genes has been identified (e.g., see Nature 388, 394-397, 1997; Proc. Natl. Acad. Sci. USA 95, 588-593, 1998; Blood 91, 4020-4027, 1998; Gene 231, 59-65, 1999) and 10 members of human TLR family (TLR1-10) have been reported so far. The role of TLR family is to recognize discrete pathogen-associated molecular patterns (PAMPs) as a pattern recognition receptor (PRR) recognizing common bacterial structure, to trigger the activation of similar intracellular signaling pathway leading to nuclear translocation of a transcription factor, NF-κB. The signaling pathway ultimately culminates in the production of inflammatory cytokines to evoke host defense responses and further evoke host defense responses to acquired immunity. Moreover, various TLR ligands are reported recently.

TLR1 recognizes triacylated lipoproteins (e.g., see J. Immunol. 169, 10-14, 2002). TLR2 recognizes a variety of bacterial components such as peptidoglycan (PGN), bacterial triacylated lipoproteins, mycoplasmal diacylated lipoproteins, and GPI anchor of Trypanosoma cruzi (e.g., see Science 285, 732, 1999; Science 285, 736, 1999; J. Biol. Chem. 274, 33419, 1999; Immunity 11, 443, 1999; J. Immunol. 164, 554, 2000; Nature 401, 811, 1999; J. Immunol. 167, 416, 2001; Nat. Med. 8, 878-884, 2002). TLR3 is involved in recognition of double-stranded RNA, which is generated in the life cycle of RNA viruses (e.g., see Immunity 11, 443-451, 1999). TLR4 is a receptor for lipopolysaccharide (hereinafter LPS), a glycolipid specific to Gram-negative bacteria cell wall (e.g., see Nature 413, 732-738, 2001; J. Immunol. 162, 3749-3752, 1999). TLR5 recognizes flagellin, a protein component of bacterial flagella (e.g., see Science 282, 2085-2088, 1998). TLR6 is required for recognition of diacylated lipoproteins (e.g., see Nature 410, 1099-1103, 2001), whereas TLR7 is crucial for recognition of imidazoquinoline, an antiviral synthetic compound, and its derivative, R-848 (e.g., see Int. Immunol. 13, 933-940, 2001). TLR9 is a receptor for DNA with bacterial unmethylated CpG motif (5'-Pu-Pu-CpG-Pyr-Pyr-3') (e.g., see Nat. Immunol. 3, 196-200, 2002).

Intracellular signaling pathways of TLRs are elicited from the TIR domain, which is conserved among the cytoplasmic regions of TLRs. A cytoplasmic molecule, MyD88, contains a TIR domain and a death domain. The death domain of MyD88 is required for interaction with other death domain-containing molecules such as IRAK-1 and IRAK-4 (e.g., see Nature 408, 740-745, 2000; Immunity 7, 837-847, 1997; Moll. Cell. 11, 293-302, 2003). The TIR domain is reportedly required for formation of dimers with other TIR domain-containing receptors or adaptors. Indeed, MyD88-deficient mice show neither splenocyte proliferation nor production of proinflammatory cytokines in response to all TLR ligands and IL-1, suggested that MyD88 is essential for the immune responses of all TLRs and the IL-1 receptors (e.g., see Immunity 9, 1, 143-150, 1998). However, a TLR3 ligand, poly (I:C), and a TLR4 ligand, LPS, still stimulate the expression of spefic genes such as IFN-β, in MyD88-deficient mice. Induction of IFN-β expression leads to maturation of dendritic cells and subsequent expression of IFN-inducible genes (e.g., see J. Immunol. 167, 5887-5894, 2001; J. Immunol. 166, 5688-5694, 2001). These observations suggested that TLR signaling is composed of at least two pathways: a MyD88-dependent pathway that leads to production of proinflammatory cytokines, and a MyD88-independent pathway associated with induction of IFN-inducible genes and maturation of dendritic cells. Moreover, the specificity of the MyD88-dependent signaling pathways through all TLRs is provided by TIRAP, the second TIR domain-containing adaptor discovered (e.g., see Nat. Immunol. 2, 835-841, 2001; Nature 413, 78-83, 2001). TIRAP-deficient mice show severe defects in activation of the MyD88-dependent signaling pathway through TLR2 and TLR4, but not other TLRs (e.g., see Nature 420, 324-329, 2002; Nature 420, 329-333, 2002).

Although the precise molecular mechanisms of the MyD88-independent signaling pathways are unknown, identification of another TIR domain-containing molecule, TRIF (e.g., see J. Immunol. 169, 6668-6672, 2002; Nat. Immunol. 4, 161-167, 2003), and genetic evidence from mice carrying a mutation in this gene revealed that TRIF plays a crucial role in MyD88-independent signaling pathway shared by TLR3 and TLR4 (e.g., see Science 301, 640-643, 2003; Nature, 424, 743-748, 2003). Furthermore, recent studies showed that two noncanonical IκB kinases (IKKs), that is, IKK-ι/IKKε and TBK1/T2K, interact with TRIF, activate IRF-3 and, finally, lead to IFN-β induction (e.g., see Science 300, 1148-1151, 2003; Nat. Immunol. 4, 491-496, 2003).

To date, two more kinds of TIR domain-containing adaptors have been identified in the human genome. One is called SARM (abbreviation for SAM and ARM domain-containing protein), whose physiological function in the TLR/IL-1R signaling remains unclear (e.g., see Genomics 74, 234-244, 2001, Trends Immunol. 24, 286-290, 2003). The other is TRAM (abbreviation for TRIF-Related Adaptor Molecule, also called TIRP) (e.g., see J. Biol. Chem. 278, 24526-24532, 2003). Previous in vitro analysis indicated that ectopic expression of TRAM activates NF-κB, as does MyD88, TIRAP and TRIF. However, it did not activate the IFN-β promoter unlike TRIF. Dominant negative mutants of this protein inhibit the NF-κB activation through IL-1R, but not through TLRs. This indicated that TRAM is a specific adaptor protein in the IL-1R-mediated MyD88-dependent signaling pathway. However, the role of TRAM in vivo remains to be clarified.

The object of the present invention is to provide a non-human animal model non-responsive especially to endotoxin being Gram-negative bacteria cell wall fraction, which is useful to elucidate the function of TRAM, a TIR domain-containing TRIF-related adaptor protein; and a method for screening substances promoting or suppressing responses to ligands recognized by TLR4 with the use of the non-human animal models non-responsive to endotoxin, and the like.

The present inventors generated TRAM-deficient mice, analyzed the role of TRAM in the TLR/IL-1R signaling pathway in vivo and obtained the below knowledge.

TRAM-deficient mice showed severe defects in cytokine production, splenocyte proliferation and up-regulation of surface molecules, in response to the TLR4 ligands, but not to other TLR ligands. Furthermore, TLR4-mediated, but not TLR3-mediated, expression of IFN-β and IFN-inducible genes was inhibited in TRAM-deficient mice. In intracellular signaling, LPS-induced autophosphorylation of IRAK-1 and the early phase of NF-κB activation were intact in TRAM-deficient mice. However, no activation of IRF-3 was observed while a defect in the late phase of NF-κB activation in response to LPS, but not to poly (I:C), was observed in TRAM-deficient cells. Given that the latter event is a feature of the MyD88-independent signaling pathway, it was indicated that TRAM specifically mediates the MyD88-independent pathway of TLR4 signaling.

In TRAM-deficient mice, TLR4-mediated activation of the MyD88-dependent pathway, which is characterized by autophosphorylation of IRAK-1 and the early phase of NF-κB activation, was comparable to that of wild-type cells. However, TLR4-mediated production of proinflammatory cytokines was reduced. Similarly, TLR4-mediated production of proinflammatory cytokines was significantly reduced in mice lacking TRIF, which is essential for TLR4- and TLR3-mediated MyD88-independent pathways. As MyD88-deficient mice showed similar phenotype, activation of the MyD88-independent pathway is clearly required for induction of proinflammatory cytokines (e.g., see Science 301, 640-643, 2003, Identification of Lps2 as a key transducer of MyD88-independent TIR signaling; Nature, 424, 743-748, 2003). Therefore, in TLR4 signaling, activation of both MyD88-dependent and MyD88-independent (TRAM/TRIF-dependent) pathways is required for proinflammatory cytokine production. However, in signaling pathways of TLR2, TLR5 and TLR9, none of which activate the MyD88-independent pathway, only the activation of MyD88-dependent pathway is sufficient to induce proinflammatory cytokines (e.g., see Science 282, 2085-2088, 1998; Nat. Immunol. 3, 392-398, 2002; J. Exp. Med. 192, 595-600, 2000; Curr. Biol. 10, 1139-1142, 2000). Therefore, at present, it remains unclear why TLR4 signaling requires activation of both MyD88-dependent and TRIF-dependent pathways to induce proinflammatory cytokines. However, it has become clear that only TLR4 utilizes all of the presently characterized TIR domain-containing adaptors, that is, MyD88, TIRAP, TRIF and TRAM.

As described above, TRAM-deficient mice showed normal responses to ligands for TLR2, TLR7, TLR9 and IL-1β, but severely defective MyD88-dependent responses to the ligands recognized by TLR4. Furthermore, activation of the TLR4-mediated MyD88-independent, but not MyD88-dependent, signaling cascade was abolished in TRAM-deficient mice. Although this phenotype was reminiscent of that of TRIF-deficient mice which lack activation of MyD88-independent pathway in both TLR3 and TLR4 signaling, TRAM-deficient mice showed a normal response to TLR3 ligands. These results indicate that TRAM is an adaptor molecule that provides specificity for the MyD88-independent pathway of TLR4 signaling.

The present invention has been thus completed based on the above knowledge.

DISCLOSURE OF THE INVENTION

In other words, the present invention relates to (1) a non-human animal non-responsive to endotoxin wherein a part or a whole of TRIF-related adaptor molecule (TRAM) genes on its chromosome is deleted, a function of expressing TRAM which is expressed in a wild-type is lacked, and a responsiveness to a ligand recognized by TLR4 is specifically impaired, (2) the non-human animal non-responsive to endotoxin according to "1", which is responsive to PGN, R-848 and CpG ODN, and non-responsive to LPS, (3) the non-human animal non-responsive to endotoxin according to "1" or "2" wherein the non-human animal is a mouse.

Furthermore, the present invention relates to (4) a method for screening a substance promoting or suppressing a response to a ligand recognized by TLR4, wherein the response to the ligand recognized by TLR4 in a immunocyte derived from the non-human animal non-responsive to endotoxin according to any one of "1" to "3" is measured/estimated, with the use of the immunocyte, a test substance and the ligand recognized by TLR4, (5) a method for screening a substance promoting or suppressing a response to a ligand recognized by TLR4, wherein the response to the ligand recognized by TLR4 in the non-human animal according to any one of "1" to "3" is measured/estimated, with the use of the non-human animal, a test substance and the ligand recognized by TLR4.

BRIEF DESCRIPTION OF DRAWINGS

FIG. 1 is a set of figures showing cloning and characterization of human TRAM, and targeted disruption of mouse Tram gene. (a) Comparison of structures of human TRAM, TRIF, MyD88 and TIRAP. Domains were determined with the BLAST program. Lengths of amino acids are indicated. DD, death domain; TIR, TIR domain. (b, c) 293 cells were transiently cotransfected with 1 μg of TRAM, MyD88, TRIF or empty vector, plus 0.1 μg of NF-κB reporter (b) or the IFN-β promoter luciferase reporter (c). Then, 24 hr after transfection, luciferase activity was measured. (d) The structures of Tram gene, the targeting vector and the predicted disrupted gene. Closed box denotes coding exon. Restriction enzymes: B, BamHI. (e) Southern blot analysis of offspring from the heterozygote intercrosses. Genomic DNA was extracted from mouse tails, digested with BamHI, electrophoresed and hybridized with the radiolabeled probe shown in (d). Southern blot analysis detected a single 7.6 kb band for wild-type mice (+/+), a 2.4 kb band for homozygous mice (−/−) and both bands for heterozygous mice (+/−). (f) Cell lysates prepared from embryonic fibroblasts were immunoprecipitated and immunoblotted with anti-TRAM antibody. The same lysates was blotted with anti-actin antibody to monitor protein expression.

FIG. 2 is a set of figures showing that IL-1-induced responses are intact in TRAM-deficient cells. (a) Embryonic fibroblasts from wild-type and TRAM-deficient mice were stimulated with 100 ng/ml of IL-1β or 10 μg/ml of LPS. Supernatants were collected 24 hr later for IL-6 analysis by ELISA. Indicated values are means ±SD of triplicate samples. N.D.; not detected. (b) Embryonic fibroblasts were stimulated with 100 ng/ml of IL-1β for the indicated periods. Nuclear extracts were prepared, and NF-κB DNA-binding activity was determined by EMSA with an NF-κB-specific probe. (c) JNK activation was also determined by Western blot analysis of cell extracts with the use of anti-phospho-JNK specific antibody.

FIG. 3 is a set of figures showing reduction of TLR4-mediated MyD88-dependent responses in TRAM-deficient mice. (a) Peritoneal macrophages from TRIF-deficient mice or wild-type mice were left unstimulated or were stimulated with 10 μg/ml of peptidoglycan (PGN), 100 ng/ml of LPS, 100 nM of R-848 or 1 μM of CpG DNA in the presence of 30 ng/ml of IFN-γ. Supernatants were collected 24 hr later by ELISA for TNF-α and IL-6 analysis. Indicated values are means ±SD of triplicate samples. N.D.: not detected. (b) Peritoneal macrophages were stimulated for 24 hr with the indicated concentrations of LPS in the presence of 30 ng/ml of IFN-γ. TNF-α, IL-6, and IL-12 p40 were measured by ELISA with the use of the supernatants. Indicated values are means ±SD of triplicate samples. (c) Proliferation of splenocytes stimulated with LPS, R-848 or CpG DNA. Splenocytes were cultured for 24 hr with the indicated concentrations of LPS, R-848 or CpG DNA. Samples were pulsed with [3H]-thymidine (1 μCi) for the last 12 hr. [3H]-thymidine incorporation was measured with a scintillation counter. (d) Splenic B220+ cells were cultured with 10 μg/ml of LPS, 100 nM of R-848, or 10 μg/ml of anti-IgM antibody. After 36 hr of culture, cells were collected and stained with biotin-conjugated anti-CD69 or anti-CD86 antibody, followed by streptavidin-PE. Stained cells were analyzed on FACS Calibur with Cell Quest software.

FIG. 4 is a set of figures showing severe defects in TLR4-mediated MyD88-independent responses in TRAM-deficient mice. Bone marrow-derived dendritic cells (a) and peritoneal macrophages (b) were stimulated with 100 ng/ml of LPS (a) or 50 μg/ml of poly (I:C) (b) for the indicated periods, respectively. Total RNA (10 μg) was extracted and analyzed by Northern blot analysis for expression of the indicated probes. The same membrane was re-hybridized with a β-actin probe.

FIG. 5 is a set of figures showing the MyD88-independent pathway impaired specifically in TLR4 signaling. Peritoneal macrophages (a, c) and lung fibroblasts (b, d) were stimulated with 50 μg/ml of poly (I:C) (a, c) and 1 μg/ml of LPS (b, d) for the indicated periods, respectively. Stat1 activation was also determined by western blot analysis of cell extracts with the use of anti-phospho-Stat1 specific antibodies (a, b). Cell lysates were prepared and subjected to native PAGE. Monomeric (arrows) and dimeric (arrowheads) forms of IRF-3 were detected by Western blot analysis (c, d). Peritoneal macrophages (e) or lung fibroblasts (f) were stimulated with 100 ng/ml of LPS (e) or 50 μg/ml of poly (I:C) for the indicated periods, respectively. Nuclear extracts were prepared, and NF-κB DNA-binding activity was determined by EMSA with the use of an NF-κB-specific probe. (g) Lysates from macrophages stimulated with LPS were immnoprecipitated with the use of anti-IRAK-1 antibodies. The kinase activity of IRAK-1 was measured by in vitro kinase assay (top). The same lysates were blotted with anti-IRAK-1 antibodies (bottom). Auto indicates autophophorylation.

BEST MODE OF CARRYING OUT THE INVENTION

As for a non-human animal non-responsive to endotoxin of the present invention, there is no specific limitation as long as it is a non-human animal model, wherein a part or a whole of the Tram genes are deleted, a function of expressing TRAM which is expressed in wild-types is lacked, and responsiveness to ligands recognized by TLR4 is specifically impaired. As for ligands recognized by TLR4, lipopolysaccharide (LPS) also termed as endotoxin mainly existing as outer membrane components of Gram-negative bacteria, lipoteichoic acid (LTA) being cell wall components of Gram-positive bacteria, Mycobacterium tuberculosis lysates, the cell wall fraction of Gram-positive bacteria, and the like can be exemplified. Moreover, in the present invention, ligands recognized by TLR4 of the present invention includes for convenience, carriers carrying these ligands, and bacterial cells themselves having these ligands on the surface of the cells besides ligands recognized by TLR4 (hereinafter referred to as "ligands of the present invention").

In the present invention, non-responsiveness means that the responsiveness of living bodies, or of cells, tissues or organs composing the living body, to the stimulation by ligands of the present invention is reduced or almost deleted. Therefore, in the present invention, a non-human animal model non-responsive to endotoxin refers to animals other than human such as mice, rats and rabbits wherein the responsiveness of living bodies, or of cells, tissues or organs composing the living body, to the stimulation by ligands of the present invention is reduced or almost deleted. Moreover, as for the stimulation by ligands of the present invention, in vivo stimulation administering endotoxin to living bodies, in vitro stimulation contacting endotoxin to cells separated from living body and the like can be exemplified.

As for the non-human animal model non-responsive to endotoxin of the present invention, non-human animals non-responsive to ligands of the present invention such as bacterial components including endotoxin, lipoteichoic acids, and Mycobacterium tuberculosis lysates and the like, but responsive to PGN being a TLR2 ligand, CpG oligodeoxynucleotides (CpG ODN) being a TLR9 ligand, IL-1, phytohemagglutinin (PHA), Poly I:C being a TLR3 ligand, and synthetic compound R-848 being a TLR7 ligand, can be exemplified. Specifically a non-human animal wherein the function of Tram gene on its chromosome is lacked can be exemplified.

In the present invention, as for an animal wherein the function of Tram gene is lacked, besides TRAM$^{-/-}$ mice, for example rodents such as rats wherein the function of expressing Tram gene is lacked can be exemplified. As for the non-human animal wherein the function of expressing these Tram genes is lacked, TRAM$^{-/-}$ non-human animals generated upon Mendel's law are preferable from the point of view of being obtainable together with its wild-type littermates, with which accurate comparative experiments can be conducted. The method for generating an animal wherein the function of expressing Tram gene is lacked will be explained in the following by taking TRAM$^{-/-}$ mouse as an example.

Tram genes are obtained by amplifying mouse genomic library by PCR or the like, and the obtained gene fragments can be screened with a probe derived from mouse Tram gene. The screened Tram genes are subcloned with plasmid vectors and the like and can be identified by restriction enzyme mapping and DNA sequencing. Next, a whole or a part of the genes encoding TRAM are replaced with pMC1 neo-gene cassette and the like, and targeting vectors are generated by introducing genes such as Diphtheria-toxin A fragment (DT-A) genes or herpes simplex virus thymidine kinase (HSV-tk) genes to the 3'end.

The generated targeting vectors are linearized and introduced into ES cells by electroporation and the like for homologous recombination, and the ES cells having performed homologous recombination by antibiotics such as G418 or Gancyclovir (GANC) are selected from the homologous recombinants. Moreover, it is preferable to confirm whether the selected ES cells were the desired recombinants by Southern blot method or the like. Clones of the confirmed ES cells are microinjected into mouse blastocysts, and the mouse blastocysts are returned to recepient mice to generate chimeric mice. The chimeric mice are intercrossed with wild-type mice to obtain heterozygous mice (F1 mice: +/−), and by breeding the heterozygous mice, TRAM$^{-/-}$ mice of the present invention can be generated. Moreover, as for a method for confirming whether TRAM has been generated in TRAM$^{-/-}$ mice, for example, there is a method for examining RNA isolated from the mice obtained by the above-mentioned method, by Northern blot method or the like, or for examining TRAM expression in these mice by Western blot method or the like.

Furthermore, it can be confirmed whether the generated TRAM$^{-/-}$ mice are non-responsive to ligands of the present invention, for example as follows; by contacting LPS being a component of Gram-negative bacteria cell wall to immunocytes such as peritoneal macrophages, mononuclear cells and dendritic cells of TRAM$^{-/-}$ mice in vitro or in vivo, and then by measuring the production levels of TNF-$\alpha$, IL-6, IL-12 and the like in the cells, the proliferative response of splenocytes, the expression levels of IFN-$\beta$ and IFN-inducible genes in bone-marrow derived dendritic cells or the activation of transcription factor IRF-3; or by administering LPS being a component of gram-negative bacteria cell wall to TRAM-knockout mice by intravenous injection or the like, and then by measuring the biological activity of endotoxin such as pyrexia, shock, reduction of leukocytes or platelets, hemorrhagic necrosis in bone marrow, hypoglycemia, IFN induction, activation of B-lymphocytes (bone marrow-derived immune response cells).

Non-human animal models of the present invention non-responsive to endotoxin or immunocytes such as macrophages, splenocytes and dendritic cells derived from the animal models, can be used for elucidating the action mechanism of TLR4 as well as screening substances promoting or suppressing the responses to TLR4 ligands, or the like. As for a method for screening substances promoting or suppressing the responses to ligands of the present invention, there is no specific limitation as long as it is a method for screening to measure/estimate the responses to ligands of the present invention in immunocytes derived from non-human animal models of the present invention, with the use of the immunocytes, a test substance, and ligands of the present invention; or a method for screening to measure/estimate the responses to ligands of the present invention in the non-human animal models of the present invention, with the use of the non-human animal models of the present invention, a test substance, and ligands of the present invention. The embodiment of the screening methods of the present invention will be explained in the following by referring to the examples.

The following methods can be exemplified: a screening method comprising the steps to culture immunocytes such as macrophages, splenocytes or dendritic cells obtained from the non-human animal models of the present invention, together with a test substance, and ligands of the present invention, and to measure/estimate the levels of cell activity in the immunocytes; a screening method comprising the steps to administer previously a test substance to the non-human animal models of the present invention, and then to culture the immunocytes obtained from the non-human animals in the presence of ligands of the present invention, and to measure/estimate the levels of cell activity in the immunocytes; a screening method comprising the steps to administer previously ligands of the present invention to the non-human animal models of the present invention, and then to culture the immunocytes obtained from the non-human animals in the presence of a test substance, and to measure/estimate the levels of cell activity in the immunocytes; and a screening method comprising the steps to administer ligands of the present invention and a test substance concurrently, or one in advance of the other, to the non-human animal models of the present invention, and to measure/estimate the levels of cell activity in the immunocytes obtained from the non-human animal model.

As for the above-mentioned method for measuring/estimating the level of cell activity in immunocytes such as macrophages and splenocytes, when the immunocytes are macrophages, a method for measuring/estimating the production levels of cytokines such as IL-6, TNF-$\alpha$ and IL-12 in macrophages, or the level of DNA binding activity of NF-$\kappa$B; and when immunocytes are splenocytes, a method for measuring/estimating the proliferation level of splenocytes or the expression levels of MHC class II in splenocytes can be exemplified, respectively. Furthermore, when measuring/estimating the level of cell activity in immunocytes, it is preferable to compare/estimate with the measurements of the wild-type non-human animal model of the non-human animal models of the present invention, especially littermates of the wild-type non-human animals as control, so that individual variety can be eliminated.

Promoting or suppressing substances obtained by the method for screening substances promoting or suppressing the responses to ligands recognized by TLR4 of the present invention or substances containing thereof are useful to elucidate the mechanism in signaling by stimulation of bacterial components in vivo, and especially promoting substances can possibly be used as preventive/treating agents for bacterial infections. When the above-mentioned promoting substances wherein preventive/treating effect for bacterial infections can be expected as pharmaceuticals are used, various prescribed compounds such as pharmaceutically acceptable normal carriers, bonding agents, stabilizing agents, excipients, diluents, pH buffer agents, disintegrators, solubilizers, dissolving adjuvants, isotonic agents can be added. Further, in a preventing or treating method by using these pharmaceuticals, appropriate dosage suited to sex, body weight and symptom of patients can be administered orally or parenterally. In other words, it can be administered orally in normal dosage forms, for example in forms of powder, granule, capsules, syrup, suspension and the like, or parenterally for example in forms of solution, emulsion, suspension and the like by injection, and moreover, it can be administered through nostril in form of spray.

The present invention will be explained specifically in the following by referring to the examples described results and methods in that order, but the technical scope of the present invention will not be limited to these.

EXAMPLE 1

Identification of the Fourth TIR Domain-Containing Adaptor, TRAM)

Figure 1:
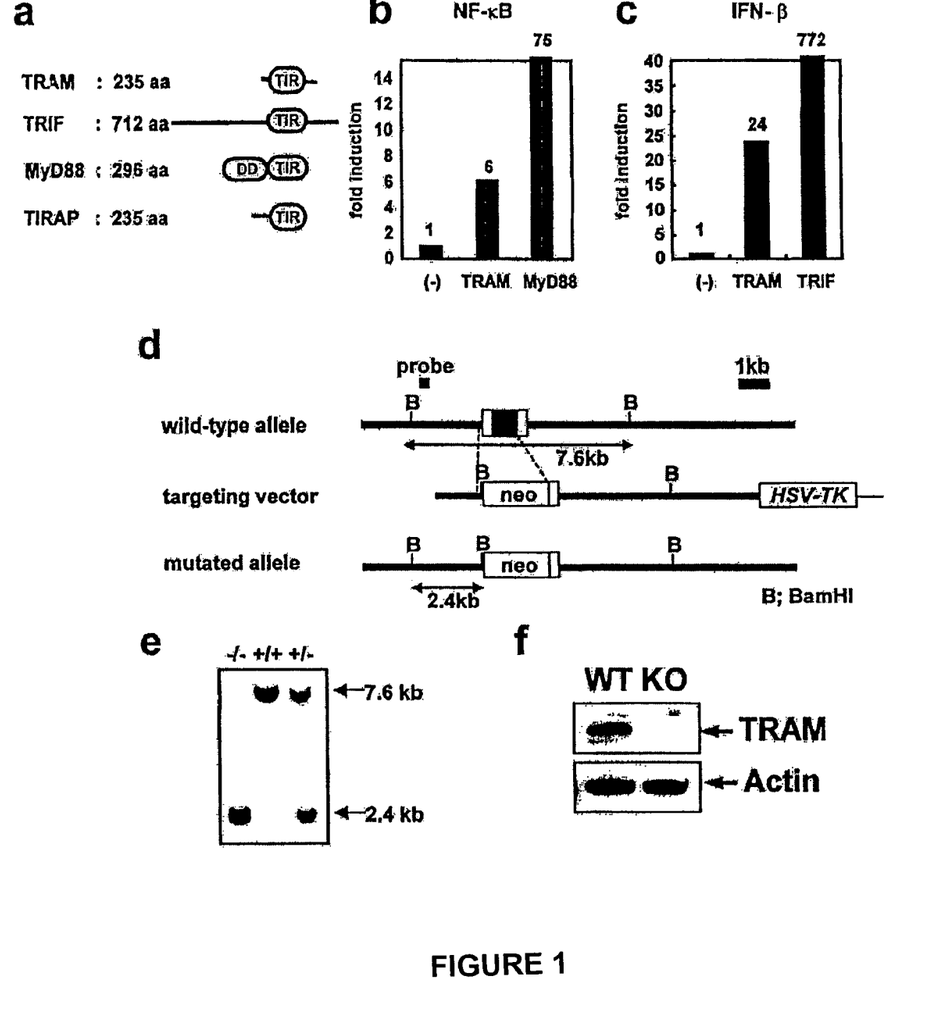

The present inventors previously identified the third TIR domain-containing adaptor, TRIF by a database search analysis (J. Immunol. 169, 6668-6672, 2002) (FIG. 1a). During this analysis, the present inventors identified another TIR domain-containing molecule. The TIR domain of this molecule showed greater homology with the TIR domain of TRIF than that of MyD88 or TIRAP. The gene of this molecule has an open reading frame of 708 bp that encodes 235 aa, and has been registered and named as TRAM for TRIF-related adaptor molecule (accession number AY232653; also known as TIRP (J. Biol. Chem. 278, 24526-24532, 2003)). Ectopic expression of TRAM in 293 cells activated NF-κB-dependent and IFN-β promoters, although at low levels compared with that of MyD88- and TRIF-mediated activation, respectively (FIGS. 1b, 1c).

EXAMPLE 2

Generation of TRAM-Deficient Mice

To elucidate the physiological role of TRAM, the present inventors generated TRAM-deficient mice by gene targeting. Mouse Tram gene consists of one exon. The present inventors constructed a targeting vector and replaced the entire exon with a neomycin-resistance gene cassette (FIG. 1d). Two correctly targeted ES clones were microinjected into C57BL/6 blastocysts to generate chimeric mice. Chimeric pup mice were crossed with female C57BL/6 mice, and the transmission of mutated alleles were monitored by Southern blot analysis (FIG. 1e). Heterozygote mice were then interbred to genarate offsprings carrying a null mutation of Tram gene. TRAM-deficient mice were born at the expected Mendelian ratio and showed no developmental abnormalities. To confirm the disruption of the Tram gene, total RNA from wild-type and TRAM-deficient lung fibroblast cells were analyzed by Northern blot. Transcripts for TRAM were not observed in TRAM-deficient mice. Immunoprecipitation analysis of splenocytes further confirmed that disruption of Tram gene abolished the expression of TRAM proteins (FIG. 1f).

EXAMPLE 3

TRAM is Not Involved in IL-1R Signaling

Figure 2:
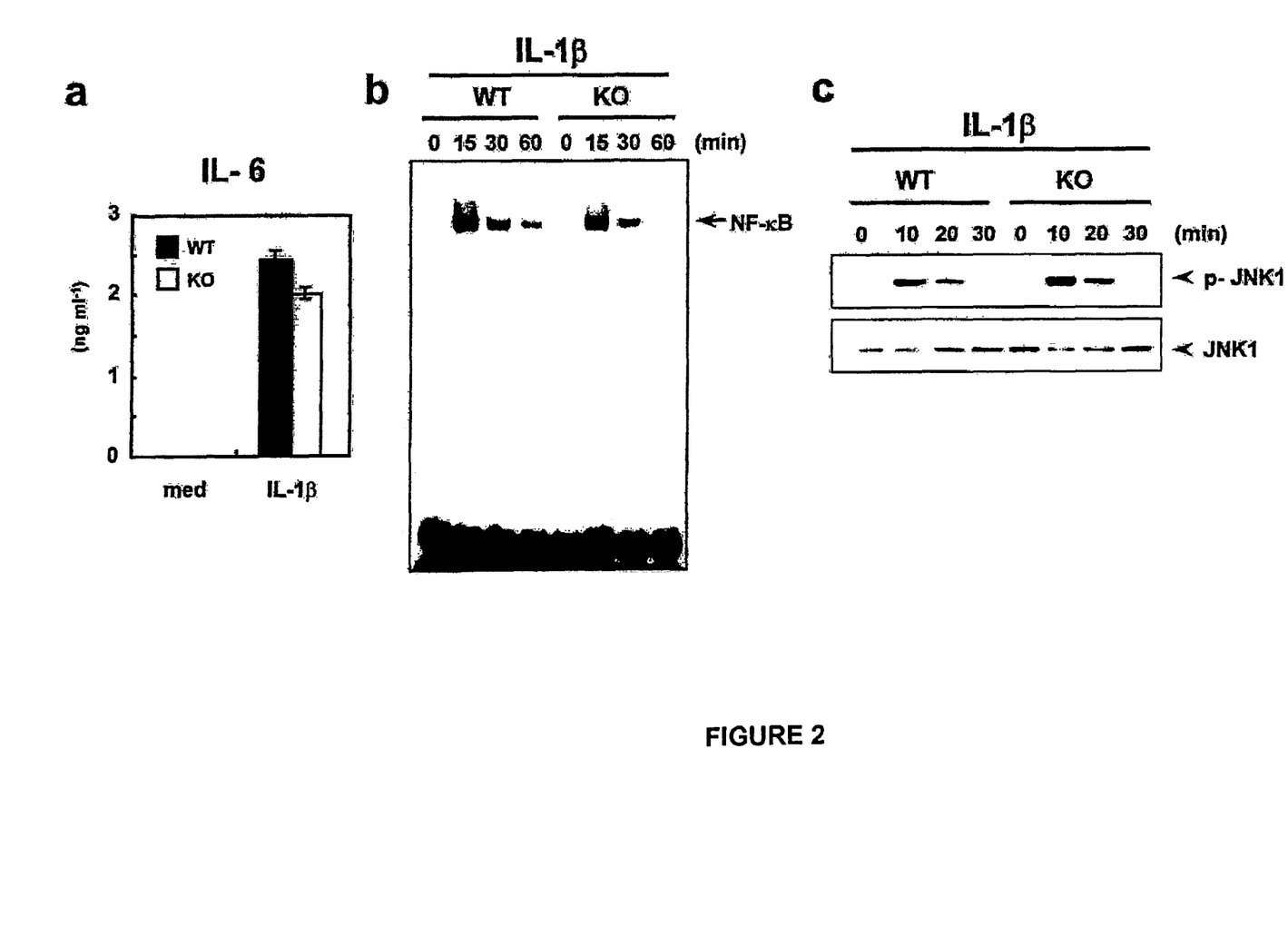

As a previous in vitro study showed that TRAM is involved in the IL-1R-mediated MyD88-dependent pathway (J. Biol. Chem. 278, 24526-24532, 2003), first it was tested whether IL-1R signaling was impaired in TRAM-deficient cells. Production of IL-6 from mouse embryonic fibroblasts (MEFs) obtained from wild-type and TRAM-deficient mice in response to IL-1β was measured by ELISA (FIG. 2a). IL-1β-induced IL-6 production was normal in TRAM-deficient MEFs. The present inventors next analyzed the activation of NF-κB and JNK1 in response to IL-1β (FIGS. 2b, 2c). IL-1β stimulation resulted in similar levels of NF-κB and JNK1 activation in both wild-type and TRAM-deficient MEFs, demonstrating that TRAM is not involved in the IL-1R-mediated signaling pathway.

EXAMPLE 4

Figure 3:
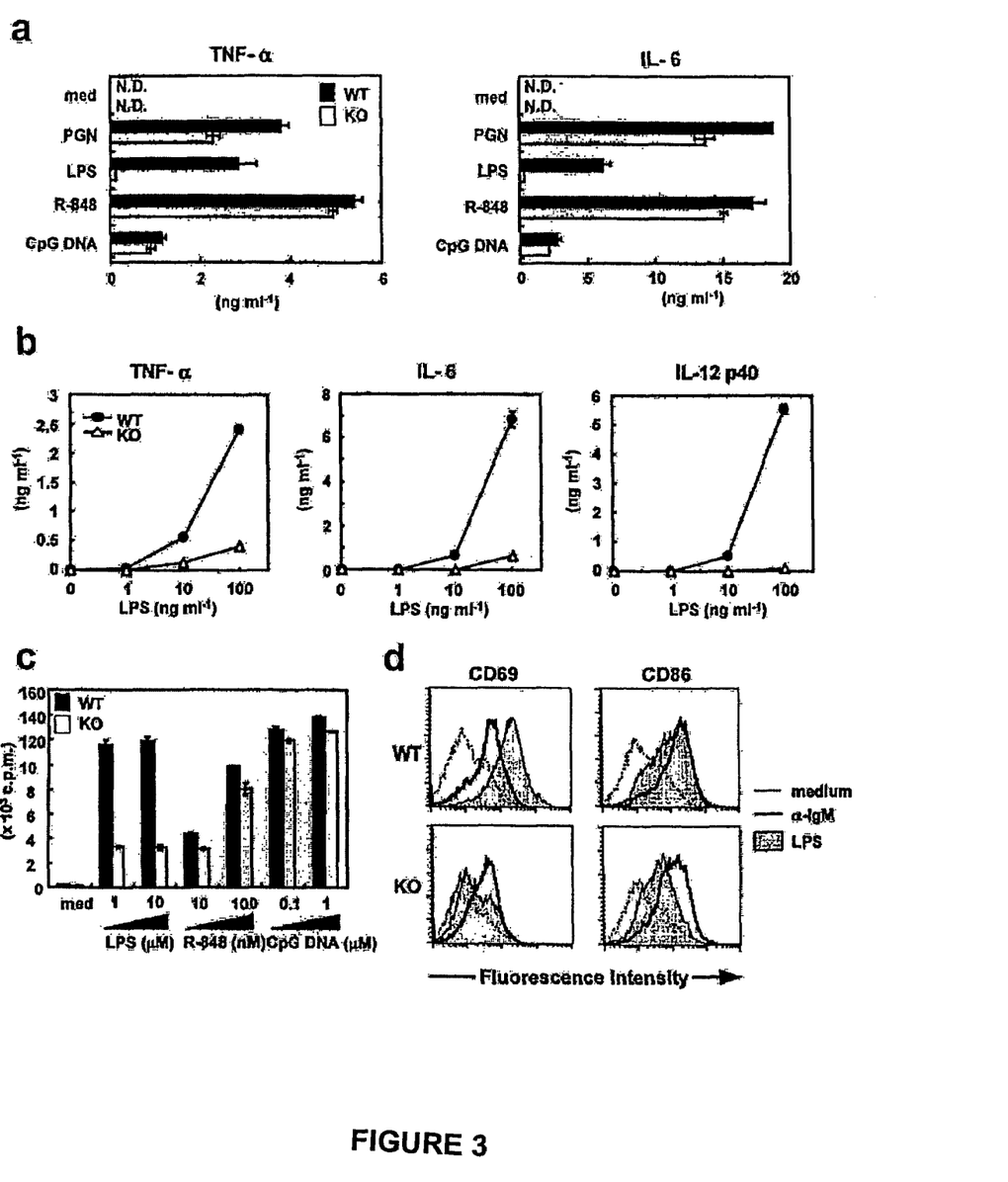

Severely Impaired TLR4-Mediated MyD88-Dependent Responses in TRAM-Deficient Mice The present inventors next analyzed the production of proinflammatory cytokines such as TNF-α or IL-6 by peritoneal macrophages in response to various TLR ligands such as PGN, LPS, R-848 and CpG DNA. PGN, R-848 or CpG DNA stimulation produced equal level of IL-6 or TNF-α in both wild-type and TRAM-deficient macrophages. However, the production of inflammatory cytokines was significantly reduced in response to LPS stimulation in TRAM-deficient cells (FIG. 3a). Wild-type cells produced TNF-α, IL-6 and IL-12p40 in response to LPS stimulation in a dose-dependent way (FIG. 3b). In contrast, LPS-induced production of TNF-α, IL-6 and IL-12p40 by LPS in TRAM-deficient cells was significantly impaired. Thus, it was revealed that TRAM-deficient mice showed defective responses in terms of LPS-induced cytokine production.

Next, the present inventors analyzed splenocyte proliferation in response to stimulation of LPS, R-848 or CpG DNA. Equal rates of splenocyte proliferation from wild-type and TRAM-deficient mice were observed in response to R-848 and CpG DNA. However, TRAM-deficient splenocytes showed defective proliferation after LPS stimulation (FIG. 3c). The present inventors next analyzed the surface expression of CD69 and CD86 on B220-positive splenocytes by FACS after stimulation with LPS or anti-IgM antibodies. Both wild-type and TRAM-deficient B220-positive cells showed comparable levels of CD69 and CD86 up-regulation in response to anti-IgM antibodies (FIG. 3d). However, LPS-induced augmentation of these molecules was significantly perturbed in TRAM-deficient cells. From these data, it became apparent that only the TLR4-mediated responses were impaired in TRAM-deficient mice.

EXAMPLE 5

Figure 4:
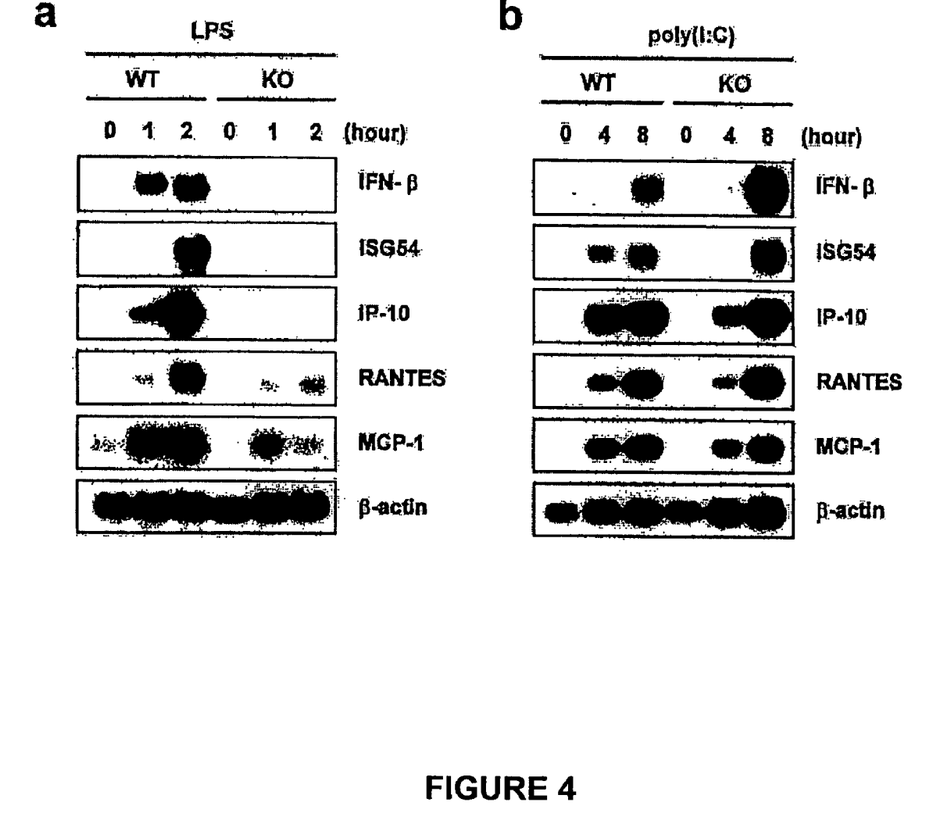

TLR4-Mediated, but Not TLR3-Mediated, MyD88-Independent Gene Expression is Severely Impaired in TRAM-Deficient Mice Ligands recognized by TLP3 and TLR4 have been shown to induce IFN-β production and to express subsequently IFN-inducible genes in a MyD88-independent way (Immunity 11, 443-451, 1999; J. Immunol. 167, 5887-5894, 2001; J. Immunol. 166, 5688-5694, 2001). As TRAM-deficient mice impair TLR4-mediated MyD88-dependent biological responses, the present inventors next investigated whether MyD88-independent responses were also impaired in these mice. The present inventors analyzed the expression of IFN-β and IFN-inducible genes in both wild-type and TRAM-deficient mice by Northern blot analysis. LPS stimulated the expression of IFN-β and IFN-inducible genes such as ISG54, IP-10, RANTES and MCP-1, in wild-type bone-marrow derived DCs. However, LPS-induced expression of these genes was severely impaired in TRAM-deficient cells (FIG. 4a). In TLR3 responses, both wild-type and TRAM-deficient peritoneal macrophages showed comparable levels of induction of these genes after poly (I:C) stimulation (FIG. 4b). These data indicated that TRAM deficiency affected not only the MyD88-dependent responses but also the MyD88-independent responses mediated by TLR4.

EXAMPLE 6

Figure 5:
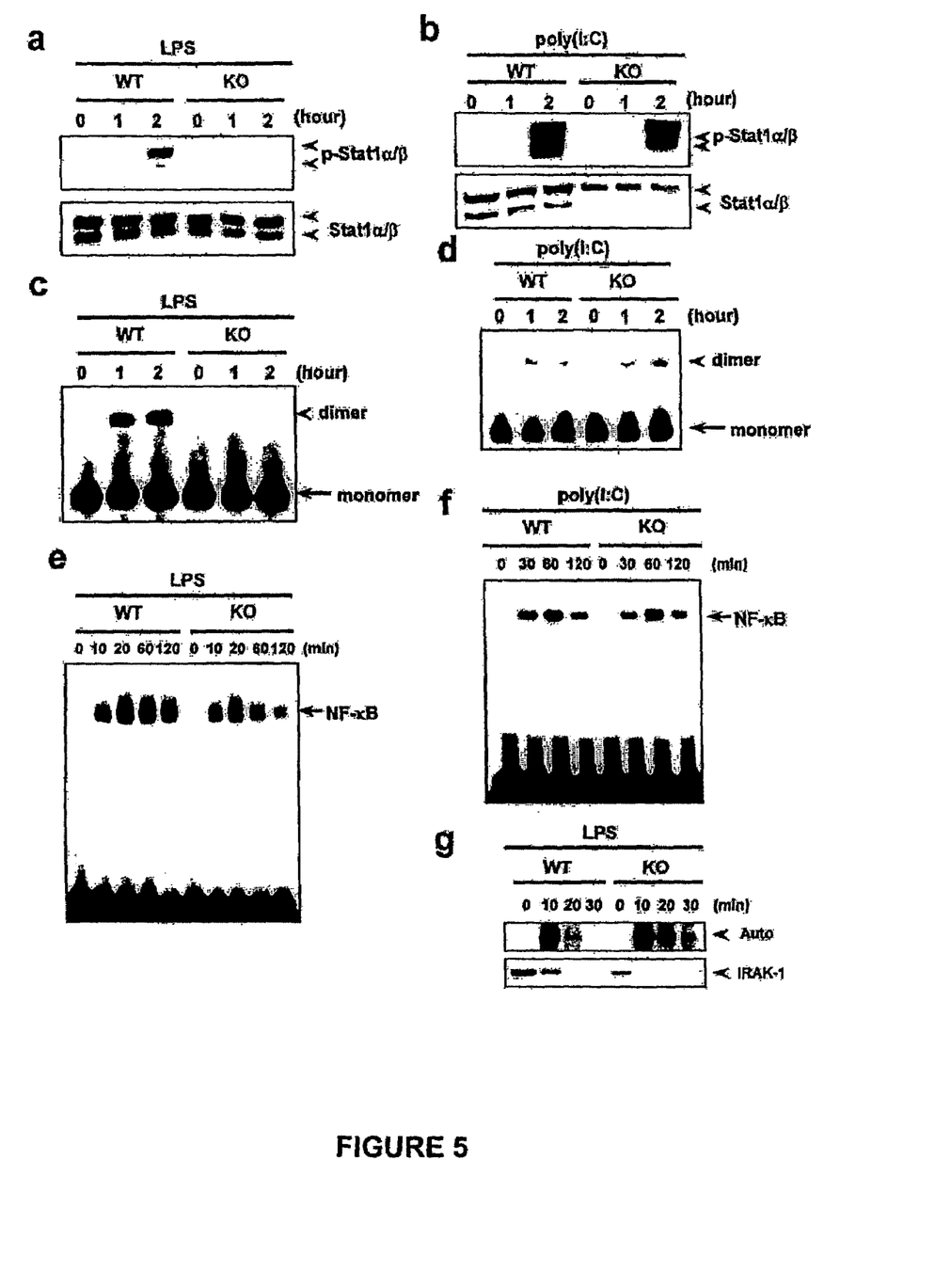

TLR4-Mediated MyD88-Independent Signaling Was Not Observed in TRAM-Deficient Mice LPS induction of IP-10 mRNA is dependent on Stat1 signaling. This was demonstrated with Stat1-deficient mice, which showed a significant reduction in IP-10 mRNA expression in LPS-stimulated macrophages compared with that of wild-type cells (J. Immunol. 163, 1537-1544, 1999; J. Leukoc. Biol. 69, 598-604, 2001; Nat. Immunol. 3, 392-398, 2002). In wild-type macrophages, 701Y of Stat1 was phosphorylated after 2 hr of LPS stimulation. However, Stat1 with tyrosine phosphorylation was not detected in TRAM-deficient macrophages (FIG. 5a). In contrast, poly (I:C) stimulation resulted in similar levels of Stat1 phophorylation in both wild-type and TRAM-deficient cells (FIG. 5b).

Given that Stat1 phosphorylation is IFN-β dependent (Nat. Immunol. 3, 392-398, 2002), the present inventors next investigated the activation of signaling molecules required for IFN-β production. The transcription factor, IRF-3 has been reported to be essential for LPS- and poly (I:C)-mediated IFN-β production. Indeed, native-PAGE analysis showed LPS-induced formation of IRF-3 homodimers in wild-type cells. However, LPS-induced IRF-3 activation was abolished in TRAM-deficient mice cells (FIG. 5c). In contrast, TRAM-deficient cells showed similar levels of IRF-3 dimer formation, compared with that of wild-type cells after ploy (I:C) stimulation (FIG. 5d). As LPS-induced Stat1 phosphorylation and IRF-3 activation are MyD88 independent, these data indicates that TLR4-mediated, but not TLR3-mediated, activation of the MyD88-independent signaling pathway is impaired in TRAM-deficient mice. TLR4-mediated MyD88-independent signaling leads to the late phase of NF-κB activation in addition to IRF-3 activation. Wild-type cells showed stable level of NF-κB activation even after 1 hr and 2 hr of LPS stimulation. In TRAM-deficient cells, LPS-induced NF-κB activation occurred normally at early time points (10 and 20 min) but gradually faded out at later time point (60 and 120 min), indicating that the late phase of NF-κB activation, which is a characteristic of TLR4-mediated MyD88-independent signaling, was severely impaired in TRAM-deficient mice (FIG. 5e). In contrast, poly (I:C)-induced NF-κB activation was observed to be normal in TRAM-deficient cells (FIG. 5f). Activation of the MyD88-dependent signaling pathway leads to IRAK-1 activation as indicated by autophosphorylation and degradation (FIG. 5g). TRAM-deficient macrophages showed LPS-induced IRAK-1 activation similarly to that of wild-type cells, indicating that activation of TLR4-mediated MyD88-dependent signaling was not impaired in TRAM-deficient mice. Taken together, these observations show that TRAM is specifically essential for the TLR4-mediated MyD88-independent signaling pathway.

EXAMPLE 7

Plasmids

The ELAM-1 promoter-derived luciferase reporter plasmid (NF-κB luciferase reporter) was provided by Dr. D. T. Golenbock. Mouse IFN-β promoter luciferase reporter was generated by PCR as described previously (Immunity 7, 837-847, 1997). Flag-tagged human TRAM was cloned into pEF-BOS vector. Expression vectors for TRIF and MyD88 were taken from the previously described reference (J. Immunol. 169, 6668-6672, 2002).

EXAMPLE 8

Luciferase Reporter Assay 293 cells were transiently cotransfected with reporter plasmids and the indicated expression vectors. Luciferase activity of total cell lysates was measured with the Dual-luciferase reporter assay system (Promega) as described previously (J. Immunol. 169, 6668-6672, 2002). The *Rennilla*-luciferase reporter gene (50 ng) was used as an internal standard.

EXAMPLE 9

Generation of TRAM-Deficient Mice

Tram genes were isolated from genomic DNA extracted from ES cells (E14.1) by PCR with the use of TaKaRa LA Taq™ (TaKaRa). The targeting vector was constructed by replacing a 1.0 kb fragment encoding the entire TRAM ORF with a neomycin-resistance gene cassette (neo), and inserting a herpes simplex virus thymidine kinase driven by a PGK promoter into the genomic fragment for negative selection (FIG. 1d). After transfecting the targeting vector into ES cells, double-resistant colonies showing resistance to G418 and gancyclovir were selected and screened by PCR and Southern blot analysis. Homologous recombinants were microinjected into C57BL/6 female mice, and heterozygous F1 offsprings were intercrossed to obtain TRAM-deficient mice. TRAM-deficient mice and their wild-type littermates from these intercrosses were used for experiments.

EXAMPLE 10

Reagents

R-848 was provided by Pharmaceuticals and Biotechnology Laboratory of Japan Energy Corporation. CpG oligodeoxynucleotides were prepared as described previously (Nat. Immunol. 3, 196-200, 2002). LPS from *Salmonella minnesota* Re 595 prepared by a phenol-chloroform-petroleum ether extraction procedure, PGN derived from *S. aureus* and poly (I:C) were purchased from Sigma, Fluka and Amersham, respectively. Anti-phospho-JNK and anti-phospho-Stat1 antibodies were purchased from Cell Signaling Technology. Anti-JNK1, anti-Stat1 and anti-actin antibodies were from Santa Cruz. Polyclonal anti-TRAM antibody was raised against amino acids 219-232 of mouse TRAM. Polyclonal anti-IRF-3 and anti-IRAK-1 antibodies were as described previously (Science 301, 640-643, 2003). Anti-IgM antibody analysis was purchased from Jackson ImmunoResearch Laboratory. FITC-labeled streptavidin, PE-conjugated anti-B220, biotin-conjugated anti-CD69, anti-CD86 and anti-I-Ab antibodies were from Pharmingen.

EXAMPLE 11

Measurement of Proinflammatory Cytokine Concentrations

Thioglycollate-elicited peritoneal macrophages were cultured in 96-well plates ($5 \times 10^4$ cells per well) with the indicated concentrations of PGN, LPS, R-848 or CpG DNA. The concentrations of TNF-α, IL-6 and IL-12 p40 in the culture supernatant were measured by ELISA according to the manufacturer's instructions (TNF-α and IL-12 p40 were from Genzyme, and IL-6 was from R&D).

EXAMPLE 12

Preparation and Analysis of Dendritic Cells

Bone-marrow cells from wild-type or TRAM-deficient mice were cultured for 6 days with 10 ng ml-1 of GM-CSF. Immature DCs were collected and analyzed.

EXAMPLE 13

Preparation of Lung Fibroblasts

Lungs from mice were excised, washed in PBS, cut into small pieces, agitated and digested enzymatically for 30 min at 37° C. Digestion buffer (10 ml/lung) was composed of 0.25% trypsin solution containing 400 nM of EDTA. Ice-cold complete DMEM medium was added to the resulting cell suspension. After centrifugation (1100 rpm for 5 min), pellets were resuspended in complete medium, and then cultured in dishes. Lung fibroblasts were used ten days after excision for each experiment.

EXAMPLE 14

Electrophoretic Mobility Shift Assay

Peritoneal macrophages and lung fibroblasts ($1 \times 10^6$) were stimulated with 100 ng/ml of LPS and 50 μg/ml of poly (I:C) for the indicated periods, respectively. Nuclear extracts were purified from cells and incubated with a probe specific for NF-κB DNA-binding site, electrophoresed, and visualized by autoradiography as described previously (Immunity 9, 1, 143-150, 1998).

EXAMPLE 15

Splenocyte Proliferation Assay

Splenocytes ($1 \times 10^5$) were cultured in 96-well plates for 24 hr with the indicated concentrations of LPS, R-848 or CpG DNA. Samples were pulse-labeled with 1 microcurie of [3H]-thymidine for the last 12 hr, and then [3H] uptake was measured in a β-scintillation counter (Packard).

EXAMPLE 16

Western Blot Analysis and in Vitro Kinase Assay

Peritoneal macrophages ($2 \times 10^6$), embryonic fibroblasts ($1 \times 10^6$) and lung fibroblasts ($1 \times 10^6$) were stimulated for the indicated periods with 100 ng/ml of LPS, 10 ng/ml of IL-10 and 50 μg/ml of poly (I:C), respectively. The cells were then lysed in a lysis buffer containing 1.0% Nonidet-P 40, 150 mM of NaCl, 20 mM of Tris-Cl (pH 7.5), 1 mM of EDTA and a protease inhibitor cocktail (Roche Diagnostics). The cell lysates were dissolved by SDS-PAGE and transferred onto a PVDF membrane (Bio-Rad). The membrane was blotted with specific antibodies, and samples were visualized with an enhanced chemiluminescence system (Perkin Elmer Life Sciences). IRAK-1 activity in the cell lysates was measured by in vitro kinase assay as described previously (Immunity 13, 539, 2000).

EXAMPLE 17

Flow Cytometric Analysis

Two million splenocytes were cultured with 50 μg/ml of poly (I:C), 10 μg/ml of LPS or 10 μg/ml of anti-IgM antibody. After 36 hr of culture, cells were collected and stained with PE-conjugated anti-B220 antibody and biotin-conjugated anti-CD69, CD86 or I-Ab antibody, followed by streptavidin-FITC. Stained cells were analyzed on FACS Calibur with Cell Quest software (Becton Dickinson).

EXAMPLE 18

Native PAGE Assay

Lung fibroblasts ($1 \times 10^6$) and peritoneal macrophages ($5 \times 10^6$) were stimulated for the indicated periods with 50 μg/ml of poly (I:C) and 1 μg/ml of LPS, respectively, and then lysed. Cell lysates in native PAGE sample buffer (62.5 mM of Tris-Cl, pH6.8, 15% glycerol and 1% deoxycholate) were separated on a native PAGE, and then immunoblotted with anti-IRF-3 antibody as described previously (Immunity 13, 539, 2000).

INDUSTRIAL APPLICABILITY

As the non-human animal models non-responsive to endotoxin such as the TRAM-knockout mice of the present invention are non-responsive to ligands recognized by TLR4 such as endotoxin, substances promoting or suppressing responses to ligands recognized by TLR4 can be screened, and therefore useful information to develop medical substances for diseases such as endotoxin shock caused by overproducing endotoxin or receptor thereof, and the like can be obtained.

The invention claimed is:

1. A transgenic homozygous TRAM-knock out mouse non-responsive to endotoxin wherein a part or a whole of TRIF-related adaptor molecule (TRAM) genes on its chromosome is deleted, a function of expressing TRAM which is expressed in a wild-type is lacked, and responsiveness to a ligand recognized by TLR4 is specifically impaired.

2. The transgenic homozygous TRAM-knock out mouse non-responsive to endotoxin according to claim 1, which is responsive to PGN, R-848 and CpG ODN, and non-responsive to LPS.

3. A method for screening a substance promoting a response to a ligand recognized by TLR4, wherein a test substance is administered to an immunocyte derived from the knock out mouse of claim 1 or 2 and to an immunocyte derived from a wild-type mouse, and wherein the following responses (a) to (c) to the ligand recognized by TLR4 are measured:
    (a) cytokine (TNFα, IL-6 and IL-12p40) production of macrophage;
    (b) splenocyte proliferation, and up-regulation of surface molecules; and
    (c) expression of signaling molecules inducing IFN-β production;
wherein a response for one or more of (a), (b), or (c) in the immunocyte derived from said wild-type mouse but not in the immunocyte derived from said knock out mouse indicates that the test substance promotes a response to a ligand recognized by TLR4.

4. A method for screening a substance promoting a response to a ligand recognized by TLR4, wherein a test substance is administered to the knock out mouse of claim 1 or 2 and to a wild-type mouse, and wherein the following responses (a) to (c) to the ligand recognized by TLR4 are measured:
    (a) cytokine (TNFα, IL-6 and IL-12p40) production of macrophage;
    (b) splenocyte proliferation, and up-regulation of surface molecules; and
    (c) expression of signaling molecules inducing IFN-β production;
wherein a response for one or more of (a), (b), or (c) in said wild-type mouse but not in said knock out mouse indicates that the test substance promotes a response to a ligand recognized by TLR4.

5. An immunocyte from the transgenic homozygous TRAM-knock out mouse non-responsive to endotoxin according to claim 1 or 2.

* * * * *